(12) United States Patent
Oreste et al.

(10) Patent No.: US 8,193,166 B2
(45) Date of Patent: Jun. 5, 2012

(54) EPIMERIZED DERIVATIVES OF K5 POLYSACCHARIDE WITH A VERY HIGH DEGREE OF SULFATION

(75) Inventors: Pasqua Anna Oreste, Milan (IT); Giorgio Zoppetti, Milan (IT)

(73) Assignee: Glycores 2000 S.r.l., Milan (IT)

( * ) Notice: Subject to any disclaimer, the term of this patent is extended or adjusted under 35 U.S.C. 154(b) by 0 days.

(21) Appl. No.: 12/895,894

(22) Filed: Oct. 1, 2010

(65) Prior Publication Data

US 2011/0021766 A1    Jan. 27, 2011

Related U.S. Application Data

(63) Continuation of application No. 10/518,302, filed as application No. PCT/IB03/02338 on Jun. 17, 2003, now Pat. No. 7,838,644.

(30) Foreign Application Priority Data

| Jun. 18, 2002 | (IT) | ............................. | MI2002A1345 |
| Jun. 18, 2002 | (IT) | ............................. | MI2002A1346 |
| Aug. 27, 2002 | (IT) | ............................. | MI2002A1854 |

(51) Int. Cl.
| C08B 37/10 | (2006.01) |
| C07H 19/00 | (2006.01) |
| C07H 21/00 | (2006.01) |
| C07H 21/02 | (2006.01) |
| A61K 31/727 | (2006.01) |
| C07H 5/04 | (2006.01) |
| C07H 5/06 | (2006.01) |

(52) U.S. Cl. .......................................... 514/56; 536/21
(58) Field of Classification Search ........................ None
See application file for complete search history.

(56) References Cited

U.S. PATENT DOCUMENTS

| 5,071,969 | A | 12/1991 | Van Boeckel et al. |
| 5,798,356 | A | 8/1998 | Doshi |
| 6,388,060 | B1 | 5/2002 | Guo et al. |
| 7,838,644 | B2 | 11/2010 | Oreste et al. |
| 2002/0062019 | A1 | 5/2002 | Oreste et al. |
| 2003/0232785 | A1* | 12/2003 | Manoni et al. ........... 514/54 |
| 2005/0027117 | A1 | 2/2005 | Oreste et al. |
| 2005/0215518 | A1 | 9/2005 | Oreste et al. |
| 2006/0014718 | A1 | 1/2006 | Oreste et al. |
| 2009/0105192 | A1 | 4/2009 | Oreste et al. |

FOREIGN PATENT DOCUMENTS

| WO | WO8203627 A1 * | 10/1982 |
| WO | 92/17507 | 10/1992 |
| WO | 96/14425 | 5/1996 |
| WO | 97/43317 | 11/1997 |
| WO | 98/42754 | 10/1998 |
| WO | 01/72848 | 10/2001 |
| WO | 02/50125 | 6/2002 |

OTHER PUBLICATIONS

Baba et al. "Novel sulfated polysaccharides: Dissociation of anti-human immunodeficiency virus activity from antithrombin activity" J. Infect. Dis. 161:208-213 (1990).
Barrowcliffe et al. "The anticoagulant activity of heparin: Measurement and relationship to chemical structure" J. Pharmaceut. & Biomed. Anal. 7:217-226 (1989).
Campbell et al. "Biosynthesis of heparin/heparan sulfate purification of the D-glucuronyl C-5 epimerase from bovine liver" J. Biol. Chem. 269:26953-26958 (1994).
Hemker et al. "Elements from in vitro studies that help understand the action of heparins" Thrombosis Res. suppl. 14:1-10 (1991).
Klein et al. "Thromboelastography as a perioperative measure of anticoagulation resulting from low molecular weight heparin: A comparison with anti-Xa concentrations" Anesth. Analg. 91:1091-1095 (2000).
Leali et al. "Fibroblast growth factor-2 antagonist activity and angiostatic capacity of sulfated *Escherichia coli* K5 polysaccharid derivatives" J. Biol. Chem. 276:37900-37908 (2001).
Lembo et al. "Sulfated K5 *Escherichia coli* polysaccharide derivatives as wide-range inhibitors of genital types of human papillomavirus" Antimicrob. Agents Chemother. 52:1374-1381 (Apr. 2008).
Naggi et al. "Toward a biotechnological heparin through combined chemical and enzymatic modification of the *Escherichia coli* K5 polysaccharide" Seminars in Thrombosis and Hemostasis 27:437-443 (2001).
Pinna et al. "Inhibition of herpes simplex virus types 1 and 2 in vitro infection by sulfated derivatives of *Escherichia coli* K5 polysaccharide" Antimicrob. Agents Chemother. 52:3078-3084 (Sep. 2008).
Razi et al. "Structural and functional properties of heparin analogues obtained by chemical sulphation of *Escherichia coli* K5 capsular polysaccharide" Biochem. J., 309:465-479 (1995).
Vicenzi et al. "Broad spectrum inhibition of HIV-1 infection by sulfated K5 *Escherichia coli* polysaccharide derivatives" AIDS 17:177-181 (Jan. 2003).

* cited by examiner

*Primary Examiner* — Layla Bland
(74) *Attorney, Agent, or Firm* — Nixon & Vanderhye P.C.

(57) ABSTRACT

A new method is described for the oversulfation of epiK5-N-sulfate to obtain an epiK5-amine-O-oversulfate with very high sulfation degree which, by subsequent N-sulfation, provides new epiK5-N,O-oversulfate-derivatives with a sulfation degree of at least 4, basically free of activity on the coagulation parameters and useful in the cosmetic or pharmaceutical field. Also described are new low molecular weight epiK5-N-sulfates useful as intermediates in the preparation of the corresponding LMW-epiK5-N,O-oversulfate-derivatives.

4 Claims, No Drawings

EPIMERIZED DERIVATIVES OF K5 POLYSACCHARIDE WITH A VERY HIGH DEGREE OF SULFATION

This application is a continuation of application Ser. No. 10/518,302, filed May 31, 2005, now U.S. Pat. No. 7,838,644; which is a U.S. national stage under 35 U.S.C. 371 of Intl Application No. PCT/IB2003/002338, filed Jun. 17, 2003; the entire contents of which are hereby incorporated by reference in this application.

OBJECT OF THE INVENTION

The present invention concerns new derivatives of K5 polysaccharide with a very high degree of sulfation, a process for their preparation, highly O-sulfated new intermediates useful in their synthesis and pharmaceutical compositions containing said derivatives of K5 polysaccharide as active ingredients basically free of activity on coagulation.

In particular, the invention refers to a process for the preparation of epiK5-N,O-oversulfates starting with a K5 polysaccharide, previously N-deacetylated, N-sulfated and C5-epimerized at least 20%, through O-oversulfation in suitable conditions and subsequent N-sulfation, to said epiK5-N,O-oversulfates of antiangiogenetic and antiviral activity and to new low molecular weight intermediates of epi-K5-N-sulfates.

BACKGROUND OF THE INVENTION

The glycosaminoglycans such as heparin, heparan sulfate, dermatan sulfate, chondroitin sulfate and hyaluronic acid are biopolymers that are industrially extracted from various animal organs.

In particular, heparin, mainly obtained by extraction from the intestinal mucous membrane of pigs or bovine lung, is a polydispersed copolymer with a molecular weight distribution from approximately 3,000 to approximately 30,000 D consisting of a chain mixture basically consisting of a uronic acid (glucuronic acid or iduronic acid) and of an amino sugar (glucosamine) linked by α-1→4 or β-1→4 bonds. In heparin, the uronic unit can be O-sulfated in position 2 and the gliucosamine unit is N-acetylated or N-sulfated, 6-O-sulfated, and 3-O-sulfated in approximately 0.5% of the gliucosamine units present.

The properties and natural biosynthesis of heparin in mammals have been described by Lindahl et al., 1986 in Lane, D. and Lindahl, U. (Editors) "Heparin. Chemical and Biological Properties; Clinical Applications", Edward Arnold, London, Pages 159-190, by Lindahl, U, Feingold D. S. and Rodén L, 1986 TIBS, 11, 221-225 and by Conrad H. E. "Heparin Binding Proteins", Chapter 2: Structure of Heparinoids. Academic Press, 1998. The biosynthesis of heparin occurs starting with its precursor N-acetyl-heparosan consisting of a chain mixture consisting of the repetitive disaccharide unit glucuronyl-β-1→4-N-acetylglucosamine. Said precursor undergoes enzymatic modifications which partially hydrolyse the N-acetyl group, substituting it with an $SO_3$— group, epimerize the carboxyl in position 5 of a part of the glucuronic units converting them into iduronic units and introducing O-sulfate groups to get a product which, once extracted industrially, has approximately double the number of sulfate groups as regards carboxyl ones per disaccharide unit. These enzymatic modifications lead to, besides, the formation of the pentasaccharide region of a bond to antithrombin III (ATIII), called active pentasaccharide, which is the structure necessary for the high affinity bond of heparin to the ATIII and fundamental for anticoagulant and antithrombotic activity of the heparin itself. This pentasaccharide, present inside only some of the chains which form heparin, contains a sulfated gliucosamine unit in position 3 and a glucuronic acid spaced out between disaccharides containing iduronic acids.

In nature, the formation of the active pentasaccharide is made possible by the epimerization reaction of the carboxyl of a part of the glucuronic units info iduronic units carried out by the glucuronyl-C5-epimerase (C5-epimerization) and by suitable sulfation which also leads to the introduction of a sulfate group onto the hydroxyl in position 3 of the glucosamine. More particularly, in nature the formation of the active pentasaccharide is made possible by the fact that the C5-epimerization occurs in clusters, i.e. on portions of chains, and extensively, which results in a product that contains more iduronic units than glucuronic ones. Commercial heparin, in fact, contains approximately 70% of iduronic units and 30% of glucuronic units. Alongside the main anticoagulant and antithrombotic activities, heparin also exercises antilipaemic, antiproliferative, antiviral, antitumorous and antimetastatic activities, but its use as a drug is hindered by the side effects due to the anticoagulant action which can cause bleeding.

PRIOR ART

It is known that the capsular K5 polysaccharide isolated from *Escherichia coli*, described by Vann W. F. et al., in European Journal of Biochemistry, 1981, 116, 359-364 ("Vann 1981"), consists of a chain mixture consisting of the repetitive disaccharide unit glucuronyl-β-1→4-N-acetyl glucosamine and therefore shows the same repetitive sequence (A)

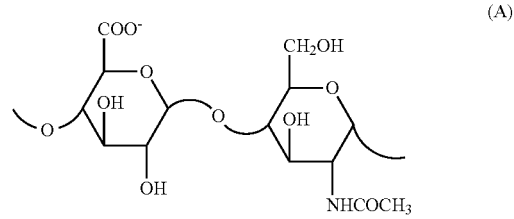

(A)

of the N-acetyl-heparosan precursor of heparin. The capsular K5 polysaccharide, referred to hereafter as "K5 polysaccharide" or more simply "K5", was chemically modified by Lormeau et al. as described in U.S. Pat. No. 5,550,116 and by Casu et al. as described in Carbohydrate Research, 1994, 263, 271-284. K5-O-sulfates having antitumorous, antimetastatic, antiviral, in particular anti-HIV activities are described in EP 333243 and WO 98/34958. The K5 was also modified chemically and enzymatically in order to obtain products having the same type of in vitro biological activity on coagulation as that of heparin as extracted from animal organs (extractive heparin).

The attainment of the products having an activity on coagulation of the same type as that of extractive heparin occurs by processes which imitate that occurring in nature and envisage the entire key step of C5-epimerization with D-glucuronyl C5 epimerase.

The processes described in IT 1230785, WO 92/17507, WO 96/14425 and WO 97/43317 utilize K5 as the starting material. K5 originating from fermentation is subjected to N-deacetylation followed by N-sulfation and on the K5-N-sulfate thus obtained C5-epimerization with C5-epimerase in solution is performed, obtained either by chromatography of a solution of microsomal enzymes from mouse mastocytoma (IT 1230 785) or from bovine liver (WO 92/17507, WO 96/14425 and WO 97/43317).

The D-glucuronyl 05 epimerase from bovine liver was purified by Campbell, P. et al. in J. Biol. Chem., 1994, 269/43, 26953-26958 ("Campbell 1994") who also supplied its composition in amino acids and described its use in solution for the transformation of a K5-N-sulfate into the corresponding 30% epimerized product, demonstrating the formation of iduronic acid by HPLC method followed by total nitrous depolymerization to disaccharide.

The document WO 98/48006 describes the DNA sequence which codes for the D-glucuronyl C5 epimerase and a recombinant D-glucuronyl C5 epimerase, obtained from a recombinant expression vector containing said DNA, afterwards purified by Campbell et al. as shown by Jin-Ping L. et al. in J. Biol Chem. 2001, 276, 20069-20077 ("Jin-Ping 2001").

The complete C5-epimerase sequence was described by Crawford B. E. et al. in J. Biol. Chem., 2001, 276(24), 21538-21543 (Crawford 2001). The document WO 01/72848 describes a method for the preparation of N-deacetylated N-sulfate derivatives of K5 polysaccharide, at least 40% epimerized of iduronic acid as regards the total of the uronic acids, having a molecular weight from 2,000 to 30,000, containing from 25 to 50% of high affinity chains for ATIII and having an anticoagulant and antithrombotic activity expressed as HCII/antiXa ratio from 1.5 to 4. Said document describes the oversulfation of a K5-N-sulfate, 40-60% epimerized and shows that the product obtained, whose $^{13}C$-RMN is illustrated, has a sulfate group content per disaccharide unit of 2-3.5. Repeating the aforesaid oversulfation in the conditions described and examining the $^{13}C$-RMN it was ascertained that the product obtained is actually a free amine whose 6-O-sulfate content is 80-95%, that of 3-O-sulfate on the amino sugar is 30%, but whose sulfation degree is 3.2. It was also observed that in the conditions of oversulfation described in WO 01/72848 a degree of sulfation higher than 3.2 was not obtained. The document US 2002/0062019 describes a process for the preparation of epiK5-N,O-sulfates, active in the control of coagulation, having a degree of sulfation from 2.3 to 2.9 and a molecular weight from 2,000 to 30,000, or from 4,000 to 8,000, or from 18,000 to 30,000. The aforesaid process involves the steps: (p-a) an N-deacetylation of K5 polysaccharide and an N-sulfation of the resulting K5-amine, (p-b) an epimerization of K5-N-sulfate, (p-c) an O-oversulfation of epiK5-N-sulfate, (p-d) a partial O-desulfation, (p-e) a selective 6-O-sulfation, (p-f) an N-sulfation of the product thus obtained, any product obtained upon termination of one of the steps (p-b)-(p-f) able to be subjected to depolymerization. Said document describes an epiK5-N,O-sulfate having a molecular weight of 7,400, obtained by the aforesaid steps (p-a)-(p-f) followed by a nitrous depolymerization at the end of step (p-f), with a degree of sulfation from 2.3 to 2.9.

The same document also describes a moiety of K5 with a molecular weight of approximately 5,000 which can also be subjected to steps (p-a)-(p-f).

In order to standardize the terminology and render the text more comprehensible, in the present description conventional terms or expressions will be used, in the singular or plural. In particular:

by "K5" or "K5 polysaccharide" is meant the capsular polysaccharide from *Escherichia coli* obtained by fermentation, i.e. a chain mixture consisting of disaccharide units (A) optionally containing a double bond at the non-reducing end as shown above, in any case, prepared and purified according to the methods described in literature, in particular according to Vann 1981, according to Manzoni M. et al., Journal of Bioactive Compatible Polymers, 1996, 11, 301-311 ("Manzoni 1996") or according to the method described in WO 01/72848 and in WO 02/068447; it is obvious for a person skilled in the art that what is shown hereafter can be applied to any N-acetylheparosan;

by "C5-epimerase" is meant the D-glucuronyl C-5 epimerase, extractive or recombinant, in any case prepared, isolated and purified, in particular as described in Campbell 1994, in WO 98/48006, in Jin-Ping L. et al. in J. Biol Chem. 2001, 276, 20069-20077 (Jin-Ping 2001") or in Crawford 2001;

by K5-amine is meant at least 95% N-deacetylated K5, but in which N-acetyl groups are undetectable with a normal NMR apparatus;

by "K5-N-sulfate" is meant at least 95% N-deacetylated and N-sulfate K5, normally 100%, since N-acetyl groups are undetectable with a normal NMR apparatus, as described hereafter;

by "epiK5" is meant the K5 and its derivatives in which 20-60% of the glucuronic units is C5-epimerized to iduronic units by "epiK5-N-sulfate" is meant K5-N-sulfate in which 20-60% of the glucuronic units is C5-epimerized to iduronic units;

by "epiK5-amine-O-oversulfate" is meant an epiK5-amine-O-sulfate with a sulfation degree of at least 3.4;

by "epiK5-N,O-oversulfate" is meant an epiK5-amine-O-sulfated completely N-sulfated with a sulfation degree of at least 4;

In addition:

the conventional terms and expressions herein defined above refer to a K5 as isolated after fermentation, generally with a molecular weight distribution from approximately 1,500 to approximately 50,000 with a mean molecular weight of 10,000-25,000, advantageously of 15,000-25,000;

the conventional terms and expressions herein defined above, when preceded by the acronym "LMW" (low molecular weight), for example LMW-K5-N-sulfate, LMW-epiK5-N-sulfate, indicate low molecular weight products, obtained by fractionation or by depolymerization of K5-N-sulfate and consisting of or derived from K5-N-sulfates having a mean molecular weight from approximately 1,500 to approximately 12,000, calculated on a 100% N-sulfated product;

the conventional terms and expressions as herein defined above, when followed by "-derivative" indicate as a whole both the derivatives from native K5 and those of low molecular weight;

by the term "approximately", referring to the molecular weight, is meant the molecular weight measured by viscometry±the theoretical weight of a disaccharide unit, including the weight of the sodium, calculated as 461 in the case of an epiK5-N-sulfate-derivative and 806 in the case of an epiK5-N,O-oversulfated-derivative with a sulfation degree of 4.35;

by the expression "preponderant species", is meant the compound which, in the mixture constituting the LMW-epiK5-N-sulfate, the LMW-epiK5-amine-O-oversulfate or the LMW-epiK5-N,O-oversulfate, is the most represented type, determined by the peak of the curve of the molecular weight measured by HPLC;

unless otherwise specifically stated, by "degree of sulfation" is meant the $SO_3$—/COO— ratio, expressible also as the number of sulfate groups per disaccharide unit, measured with the conductometric method described by Casu B. et al. in Carbohydrate Research, 1975, 39, 168-176 (Casu 1975), the same utilized in WO 01/72848;

by "conditions of O-oversulfation" is meant an extreme O-sulfation performed, for example, according to the Method C described by B. Casu et al. in Carbohydrate Research, 1994, 263, 271-284 (Casu 1994);

by the term "alkyl" is meant a linear or branched alkyl, whereas "tetrabutylammonium" denotes the tetra-n-butylammonium group.

SUMMARY OF THE INVENTION

It has now surprisingly been found that, unlike that which occurs with the processes described in IT 1230785, WO 92/17507, WO 96/14425, WO 97/43317, WO 01/72848 and US 2002/0062019, starting with an epiK5-N-sulfate it is possible to obtain an epiK5-amine-O-oversulfate with a greater degree of sulfation than every other epiK5-amine-O-sulfate described in literature, for example in WO 01/72848, by preparing the salt with tertiary or quaternary organic base of said epiK5-N-sulfate taking care to let the reaction mixture to stand for a time period of 30-60 minutes maintaining the pH at approximately 7 with the same organic base and then treating the salt obtained with an O-sulfation reagent in the conditions of O-oversulfation.

Subjecting the epiK5-amine-O-oversulfates thus obtained to N-sulfation, new epiK5-N,O-oversulfates are obtained which, unlike the products described in IT 1230785, WO 92/17507, WO 96/14425, WO 97/43317, WO 01/72848 and US 2002/0062019, are free of activity on coagulation and useful for the preparation of medicines, particularly pharmaceutical compositions of antiangiogenetic and antiviral activity or of cosmetic compositions.

By depolymerization with nitrous acid of said epiK5-N,O-oversulfates new LMW-epiK5-N,O oversulfates are obtained, free of activity on coagulation, and with antiangiogenetic and antiviral activity.

In preparing N,O-sulfate N-deacetylated derivatives of K5 polysaccharide, at least 40% epimerized of iduronic acid as regards the total of the uronic acids and having low molecular weight according to the method described in WO 01/72848, it was ascertained that the depolymerization of the product of high molecular weight obtained at the end of the final N-sulfation step of the process can give varying results since it generally produces some depolymerized products showing much lower activity, than that of high molecular weight products from which they arise, on all the coagulation parameters. It is assumed this takes place because degradation with nitrous acid is influenced by the presence of the sulfate groups. In particular the sulfates in position 3 of the glucosamine result in heterogenous products, as described by Nagasawa et al. in Thrombosis Research, 1992, 65, 463-467 (Nagasawa 1992).

It has now been found that subjecting an epiK5-N-sulfate to nitrous depolymerization in which the iduronic acid content as regards the total of uronic acids is 20-60%, advantageously of 40-60%, preferably around 50%, LMW-epiK5-N-sulfates are obtained which constitute new effective intermediates for the preparation of LMW-epiK5-N,O-oversulfates having a high degree of activity on different biological parameters, with or without activity on coagulation parameters. In particular, it was found that it is possible to depolymerize an epiK5-N-sulfate so as to obtain new LMW-epiK5-N-sulfates of mean molecular weight from approximately 2,000 to approximately 4,000, more particularly specific LMW-epiK5-N-sulfates consisting of mixtures in which the predominant compound is a decasaccharide or a dodecasaccharide or a tetradecasaccharide. Also these LMW-epiK5-N-sulfates, otherwise unobtainable, have interesting biological properties and are useful intermediates for the preparation of LMW-epiK5-N,O-oversulfated of antiviral and/or antiangiogenetic activity and surprisingly free of activity on coagulation.

By subjecting a LMW-epiK5-N-sulfate to the aforesaid method of salification with a tertiary or quaternary organic base, taking care to let the reaction mixture to stand for a time period of 30-60 minutes maintaining the pH at approximately 7 with the same organic base and then treating the salt obtained with an O-sulfation reagent in the conditions of O-oversulfation, new LMW-epiK5-amine-O-oversulfates are obtained. By subjecting the LMW-epiK5-amine-O-oversulfate to N-sulfation, new N-sulfated and O-oversulfated derivatives (LMW-epiK5-N,O-oversulfates) are obtained, surprisingly free of activity on coagulation and of antiviral and/or antiangiogenetic activity, useful for the preparation of pharmaceutical or cosmetic compositions.

These LMW-epiK5-N-sulfates are obtained starting with a K5-N-sulfate with an epimerization reaction with an isolated and purified recombinant C5-epimerase, immobilized on a solid support, at a temperature of approximately 30° C. and at a pH of approximately 7 for 12-24 hours in the presence of a bivalent cation selected among calcium, magnesium, barium and manganese and a subsequent nitrous depolymerization reaction of the epimerized product thus obtained, or vice versa.

Surprisingly, from observations made on the course of the epimerization reaction in the aforesaid conditions, it is possible to assume that, contrary to that occurring in nature in the biosynthesis of heparin, ordinary and not "cluster" type C5-epimerization of the substrate occurs every 2 glucuronic acid units which leads to epi-K5-N-sulfate-derivatives characterized by a repetitive tetrasaccharide unit consisting of two gliucosamine units separated by a glucuronic unit and followed by an iduronic unit or vice versa.

DETAILED DESCRIPTION

Thus, according to one of its aspects, the present invention provides a process for the preparation of epiK5-N,O-oversulfate-derivatives, characterized in that
(a) a K5-N-sulfate-derivative, in acidic form, is treated with a tertiary or quaternary organic base, letting the reaction mixture to stand for a time period of 30-60 minutes, maintaining the pH of the solution at a value of 7 by addition of the same tertiary or quaternary organic base, and its salt is isolated with said organic base;
(b) said salt of organic base of said epiK5-N-sulfate-derivative is treated with an O-sulfation reagent in the conditions of O-oversulfation;
(c) the epi-K5-amine-O-oversulfate-derivative thus obtained is treated with a reagent of N-sulfation and the epiK5-N,O-oversulfate-derivative is isolated.

Generally, the epiK5-N,O-oversulfate-derivative is isolated in sodium salt form and optionally said sodium salt is transformed into another chemically or pharmaceutically acceptable salt.

In this context, the term "chemically acceptable" refers to a cation usable in chemical synthesis, such as the sodium, ammonium, $(C_1$-$C_4)$tetraalkylammonium ion, or for the purification of the product, whereas "pharmaceutically acceptable" is self-explanatory. Advantageous cations are those derived from alkaline metals, alkaline-earth metals, ammonium, $(C_1-C_4)$tetraalkylammonium, aluminum and zinc. Preferred cations are the sodium, calcium and tetrabutylammonium ions.

According to an advantageous manner of procedure, step (a) is carried out by passing a solution of the sodium salt of epiK5-N-sulfate-derivative, i.e. of K5 polysaccharide, previously N-deacetylated, N-sulfated, normally 100%, and 20-60% C5-epimerized and optionally depolymerized with nitrous acid, having a mean molecular weight from approximately 1,000 to approximately 25,000, advantageously from approximately 1,500 to approximately 25,000, through an acid ionic exchange resin, for example of the type IR-120 $H^+$, collecting the eluate also including the washing water of the resin and neutralizing the eluate with tertiary or quaternary organic base, preferably with an aqueous solution of tetrabutylammonium hydroxide. The solution is let to stand for 1 hour, maintaining its pH at 7 by addition of the same base and the salt thus obtained is isolated by lyophilization.

In step (b), the 0-oversulfation occurs by using an excess of O-sulfating agent and working at a temperature from 20 to 70° C. for a time period of up to 24 hours in an aprotic polar solvent.

Advantageously, the salt with a tertiary or quaternary organic base of the epiK5-N-sulfate-derivative, i.e. of K5 polysaccharide, previously N-deacetylated, N-sulfated preferably 100%, and 20-60% C5-epimerized and optionally depolymerized with nitrous acid, having a mean molecular weight from approximately 1,000 to approximately 25,000, advantageously from approximately 1,500 to approximately 25,000 as isolated in step (a), is dissolved in dimethylformamide and treated with 2-10 moles of an O-sulfation reagent for every free hydroxyl at a temperature of 40-60° C. for 10-20 hours. As an O-sulfation reagent is advantageously used the pyridine. $SO_3$ adduct in a quantity of 2.5-5 moles, preferably 2.5-4 moles per free hydroxyl per disaccharide and the reaction is advantageously carried out at 50-60° C., preferably at 55° C., overnight. The product obtained upon termination of the reaction is isolated by addition of 0.1-1 volume of water and neutralization, preferably with sodium hydroxide, precipitation with a saturated sodium chloride solution in acetone, filtration and possible ultrafiltration.

The product thus obtained is generally the sodium salt of an epiK5-amine-O-oversulfate-derivative having an iduronic acid content of 20-60% of the total of the uronic acids, having a mean molecular weight from approximately 3,500 to approximately 40,000, advantageously from approximately 4,500 to approximately 40,000 and a sulfation degree of at least 3.4, advantageously of at least 3.5, more advantageously from 3.55 to 4, preferably from 3.55 to 3.8. The sodium salt thus obtained can be converted into another salt. By way of example an exchange with the calcium ion can be performed working with ultrafiltration membranes.

In step (c), the epiK5-amine-O-oversulfated-derivative with a very high degree of sulfation is N-sulfated using the known N-sulfation methods in literature.

In practice, the N-sulfation is performed by treating an aqueous solution containing the epiK5-amine-O-oversulfated-derivative originating from step (b) with sodium carbonate and an agent of N-sulfation, for example a $(C_1-C_4)$ trialkylamine.$SO_3$ or pyridine.$SO_3$ adduct, maintaining the mixture at 30-50° C. for 8-24 hours and isolating the desired epiK5-N,O-oversulfate-derivative, for example by diafiltration. Optionally the step of N-sulfation is repeated until obtaining more than 95% substitution, preferably complete.

The new epiK5-N,O-oversulfate-derivatives thus obtained are generally in their sodium salt form. Said sodium salt can be converted into another chemically or pharmaceutically acceptable salt. Particularly advantageous salts are those of alkaline metals, alkaline-earth metals, of ammonium, $(C_1-C_4)$tetraalkylammonium, aluminum and zinc. Preferred are the salts of sodium, calcium and tetrabutylammonium.

The starting epiK5-N-sulfates subjected to step (a) of the process of the present invention are derived from a K5 polysaccharide, previously N-deacetylated, N-sulfated virtually 100%, and 20-60% C5-epimerized, advantageously 40-60%, and optionally depolymerized with nitrous acid, having a mean molecular weight from approximately 1,000 to approximately 25,000, advantageously from approximately 1,500 to approximately 25,000. Preferably, said starting material is an epi-K5-N-sulfate having a mean molecular weight between 10,000 and 25,000 or a LMW-epiK5-N-sulfate having a mean molecular weight from approximately 1,000 to approximately 12,000, advantageously from approximately 1,000 to approximately 10,000, preferably between approximately 1,500 and approximately 8,000.

The epiK5-N-sulfates, prepared by C5-epimerization of K5-N-sulfates, are well known in literature and widely described for example in WO 92/17507, WO 01/72848, WO 98/14425, WO 97/43317 or US 2002/0062019. Their preparation by C-5 epimerization of the glucuronic unit of K5-N-sulfate with a D-glucuronyl C5 epimerase was described in documents cited herein above.

A LMWepiK5-N-sulfate having an iduronic unit content of approximately 20%, obtained by N-deacetylation, N-sulfation and C5-epimerization of a moiety of K5 having a mean molecular weight of 5,000 is described in WO 92/17507. However such LMW-K5-N-sulfate contains a considerable quantity of acetyl groups.

An epiK5-N-sulfate with an iduronic acid content of 40-60%, particularly advantageous as a starting material, is that obtained by epimerization of a K5-N-sulfate virtually free of acetyl groups, in turn prepared from particularly pure K5, in particular not containing lipophilic substances, described in WO 02/068477. According to a preferential manner of procedure, by epimerization a K5-N-sulfate is used obtained from a K5 free of lipophilic substances like that described in WO 02/068477 and the C5 epimerization is performed with a D-glucuronyl C5-epimerase that is isolated, purified and immobilized on a solid support, at a pH of approximately 7, at a temperature of approximately 30° C. and for a time period of 12-24 hours in the presence of at least one bivalent ion selected among calcium, magnesium, barium and manganese.

The LMW-epiK5-N-sulfates having a higher content of iduronic units, in particular 40-60%, preferably 50-55%, are new, particularly advantageous products as starting materials in the preparation of LMW-epiK5-N,O-oversulfate-derivatives.

The LMW-epiK5-N-sulfates as shown above are prepared by a process characterized in that a K5-N-sulfate is subjected, in any one order,
(i) to C5-epimerization with a D-glucuronyl C5-epimerase that is isolated, purified and in solution or immobilized on a solid support, at a pH of approximately 7, at a temperature of approximately 30° C. and for a time period of 12-24 hours in the presence of at least one bivalent ion selected among calcium, magnesium, barium and manganese; and
(ii) to a nitrous depolymerization optionally followed by reduction, normally with sodium borohydride.

The expression "in any order" shows that the process can be indifferently carried out both in the direction (i)-(ii), i.e. in the sequence shown above, as well as in reverse direction, i.e. also in the direction (ii)-(i), subjecting the K5-N-sulfate at first to the nitrous depolymerization reaction, optionally followed by reduction with sodium borohydride, and afterwards to C5-epimerization in the aforesaid conditions. The preferred order is in the direction (i)→(ii). The sequence (ii)-(i) is preferably utilized starting with LMW-K5-N-sulfates having a mean molecular weight of more than 4,000, preferably starting with approximately 6,000. For example, one can determine the amount of sodium nitrite which, starting with 1 g of epiK5-N-sulfate, allows the attainment of a LMW-epiK5-N-sulfate with a molecular weight of more than 4,000, in particular of at least 6,000, so as to obtain useful intermediates for the preparation of LMWepiK5-N,O-oversulfates. In fact, in this case, in step (ii) the percentage of optimum epimerization is obtained.

According to a preferential aspect of the invention, the C5-epimerase is immobilized on an inert solid support.

The C5-epimerase, preferably recombinant, isolated and purified for example according to Campbell 1994, WO 98/48006, Jin-Ping 2001 or Crawford 2001, is immobilized on an inert support in the presence of the substrate, i.e. in the presence of starting K5-N-sulfate-derivative or in the presence of LMW-K5-N-sulfate, advantageously having a mean molecular weight of more than 4,000, preferably of at least 6,000. The immobilization is performed according to conventional methods, for example as described in WO 01/72848.

The C-5epimerization reaction is carried out by recirculating 20-1,000 ml of a 25 mM HEPES solution at a pH of approximately 7 containing 0.001-10 g of substrate (K5-N-sulfate or LMW-K5-N-sulfate, preferably with a molecular weight of more than 4,000, in particular of at least 6,000) and a cation selected among calcium, magnesium, barium and manganese at a concentration of between 10 and 60 mM through a column containing from $1.2 \times 10^7$ to $3 \times 10^{11}$ cpm of the immobilized enzyme, maintaining the pH at approximately 7 at approximately 30° C., at a flow of 30-220 ml/hour for a time period of 12-24 hours, advantageously 15-24 hours.

Preferably said solution is recirculated at a flow of approximately 200 ml/hour overnight (15-20 hours). The product obtained is purified and separated according to known methods, for example by ultrafiltration and precipitation with ethanol. The product thus obtained is either consisting of epiK5-N-sulfate (and in such case is dissolved in water and subjected to depolymerization) or LMW-epiK5-N-sulfate (in such case it constitutes the end product). The percentage of epimerization, in practice the amount of iduronic units as regards the glucuronic ones, is calculated using $^1$H-RMN according to the method described in WO 96/4425.

The nitrous depolymerization reaction is carried out according to known methods by the depolymerization of heparin, for example according to the method described in EP 37319, in WO 82/03627 or according to the method by depolymerization of a K5-N-sulfate described in EP 544592, but starting with a K5-N-sulfate or an epiK5-N-sulfate containing from 0 to no more than 10%, preferably no more than 5%, of acetyl groups. Preferably, the depolymerization, performed with sodium nitrite and hydrochloric acid on an epiK5-N-sulfate virtually free of acetyl groups, is followed by in situ reduction with sodium borohydride.

In practice, a cold aqueous solution of epiK5-N-sulfate is brought to acid pH (approximately 2) with hydrochloric acid and, still cold, treated with sodium nitrite maintaining the temperature (approximately 4° C.) and the pH (approximately 2) constant and, upon termination of depolymerization (approximately 15-30 minutes) the solution is neutralized with sodium hydroxide and treated, still at approximately 4° C., with an aqueous solution of sodium borohydride. Upon termination of the reduction (approximately 4 hours) the excess sodium borohydride is destroyed with hydrochloric acid, the solution is neutralized with sodium hydroxide and the depolymerized (and reduced) product is isolated according to known methods, for example by straightforward precipitation with ethanol or acetone. The product obtained upon termination of depolymerization can be either a LMW-epiK5-N-sulfate (in such case it constitutes the end product) or a LMW-K5-N-sulfate (and in such case is directly subjected to C5-epimerization as herein shown above, after isolation or also in solution without being previously isolated), in particular when it has a mean molecular weight of more than 4,000, preferably of at least 6,000, or is utilized to prepare antiangiogenetic and antiviral activity LMW-K5-N,O-oversulfated. By appropriately controlling the depolymerization reaction, in particular using different amounts of sodium nitrite/hydrochloric acid, are obtained LMW-K5-N-sulfates or LMW-epiK5-N-sulfates having a mean molecular weight in the entire interval from approximately 1,500 to approximately 12,000, advantageously from approximately 1,500 to approximately 10,000, preferably from approximately 1,500 to approximately 7,500, calculated at the $^{13}$C-RMN spectrum through the integration of the signal attributed to the C2 of 2,5-anhydromannitol with that of the anomeric carbon of the glucosamine inside the polysaccharide chain. According to a general manner of procedure, starting for example with 1 g of epiK5-N-sulfate, the starting product is dissolved in 100-200 ml of deionized water and thermostated at 4° C. Then an amount of sodium nitrite is added so as to obtain the desired mean molecular weight, for example from approximately 2,000 to approximately 4,000. Therefore, starting with an epiK5-N-sulfate having a molecular weight of 20,000 measured with the HPLC method equipped with a BioRad BioSil 250 column and using a heparin standard of known molecular weight, will require the addition of 330 to 480 mg of sodium nitrite dissolved in a 0.2% aqueous solution. The solution containing the epiK5-N-sulfate and the sodium nitrite, kept at 4° C., is brought to pH 2 through the addition of 0.1 N HCl cooled to 4° C. It is left to react under slow agitation for 20-40 minutes, then is neutralized with 0.1 N NaOH. The product obtained is brought to room temperature and treated with reducing agent such as for example sodium borohydride (250-500 mg dissolved in 50-100 ml of water) and left to react for 4-8 hours. The excess sodium borohydride is eliminated bringing the pH to 5-5.5 with 0.1 N HCl and let to stand for a further 2-4 hours. In the end it is neutralized with 0.1 N NaOH and the product is recovered by precipitation with acetone or ethanol after having concentrated the product by evaporation at reduced pressure.

Similarly, the amount of sodium nitrite can be determined which, starting with 1 g of K5-N-sulfate or epiK5-N-sulfate, allows the attainment of a LMW-K5-N-sulfate or a LMW-epiK5-N-sulfate with a mean molecular weight from approximately 4,000 to approximately 12,000, advantageously from approximately 4,000 to approximately 7,500, in particular of 6,000-7,500.

The LMW-epiK5-N-sulfate thus obtained, with an iduronic acid content from 20 to 60%, advantageously from 40 to 60%, preferably of 50-55% and virtually free of $NH_2$ and N-acetyl groups, having a mean molecular weight from approximately 1,500 to approximately 12,000, advantageously from approximately 1,500 to approximately 10,000, preferably from approximately 1,500 to approximately 7,500 and their chemically or pharmaceutically acceptable salts constitute new products useful as particularly interesting starting materials in the preparation of LMW-epiK5-N,O-oversulfates, but also themselves useful as active ingredients of pharmaceutical or cosmetic compositions and constitute an additional aspect of the present invention.

Advantageously, the starting materials in the preparation of the epiK5-N,O-oversulfate-derivatives of the present invention are epiK5-N-sulfate-derivatives consisting of a chain mixture in which at least 90% of said chains have the formula I

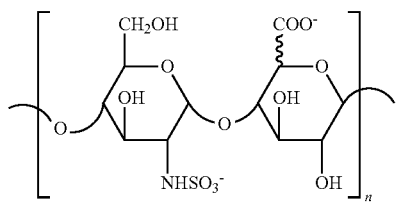

(I)

in which the uronic units are 20-60% consisting of iduronic acid, n is a integer from 2 to 100, advantageously from 3 to 100 and the corresponding cation is chemically or pharmaceutically acceptable. More advantageously, said starting epiK5-N-sulfate-derivatives are consisting of a chain mixture in which at least 90% of said chains have the formula I in which the uronic units are 40-60% consisting of iduronic acid, n is a integer from 2 to 100, advantageously from 3 to 100 and the corresponding cation is chemically acceptable. Preferred starting materials are LMW-epiK5-N-sulfates as shown above, consisting of a chain mixture in which at least 90% of said chains have the formula I in which the uronic units are 20-60% comprised advantageously 40-60%, preferably 50-55%, of iduronic acid, n is a integer from 2 to 20, advantageously from 3 to 15 and the corresponding cation is chemically acceptable.

In practice, said preferred LMW-epiK5-N-sulfates are consisting of a chain mixture in which at least 90% of said chains have the formula I'

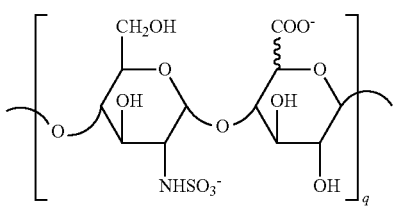

(I')

in which the uronic units are 20-60% comprised, advantageously 40-60%, preferably 50-55% of iduronic acid; q is a integer from 2 to 20, advantageously from 3 to 15, and the corresponding cation is chemically or pharmaceutically acceptable.

In this context, the term "chemically" refers to a cation usable in chemical synthesis, such as sodium, ammonium, $(C_1-C_4)$tetraalkylammonium ions, or for the purification of the product.

Advantageous cations are those derived from alkaline metals, alkaline-earth metals, ammonium, $(C_1-C_4)$tetraalkylammonium, aluminum and zinc. Preferred cations are the sodium, calcium and tetrabutylammonium ions.

Particularly interesting are the LMW-epiK5-N-sulfates consisting of a chain mixture in which at least 90% of said chains have the formula I' herein above, obtained by nitrous depolymerization of the corresponding epiK5-N-sulfates shown above and subsequent possible reduction for example with sodium borohydride, Among these, are preferred the LMW-epiK5-N-sulfates consisting of a chain mixture in which the preponderant species has the formula I'a

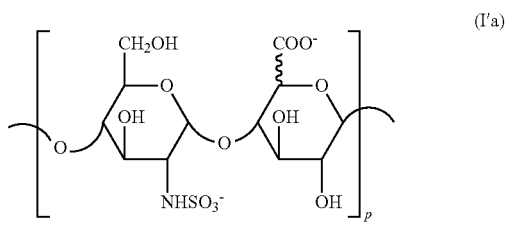

(I'a)

in which the uronic units are 60-40% consisting of glucuronic acid and 40% to 60% of iduronic acid, p is a integer from 4 to 8. The mean molecular weight of these products is from approximately 2000 to approximately 4000 and the corresponding cation is chemically or pharmaceutically acceptable.

The origin of these epiK5-N-sulfates from a step of nitrous depolymerization involves, at the reducing end of the majority of the chains in said chain mixture, the presence of a 2,5-anhydromannose unit or, in the case of reduction with for example sodium borohydride, of 2,5-anhydromannitol of structure (a)

(a)

in which X represents a formyl group or a hydroxymethyl group. Therefore, the reducing end of the majority (60-70% of the chains) is actually represented by the structure (b)

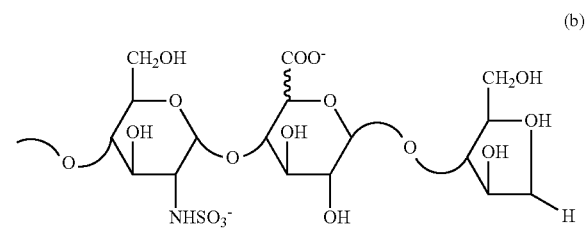

(b)

in which X is as defined above.

The presence of the structure (a) does not have any influence on the chemical characteristics of the epiK5-N-sulfates and their derivatives since any sulfations would lead to a possible introduction of one or two sulfate groups which would not however significantly move the sulfation degree of the O-sulfated derivatives. It is however preferable that the nitrous depolymerization is followed by reduction for example with sodium borohydride since, according to the process of the present invention, said LMW-epiK5-N-sulfates are subjected to sulfation and acylation reactions whose influence, of the 2,5-anhydromannose radical of structure (a), is unknown on the formyl group in which X represents formyl. Besides, the presence of structure (a) does not influence the biological activity of the products, as demonstrated by Østergaard P. B. et al. in Thrombosis Research, 1987, 45, 739-749 (Østergaard 1987) for the heparins of low molecular weight.

Particularly advantageous LMW-epiK5-N-sulfates according to the present invention are consisting of chain mixtures in which the preponderant species is a compound of formula I'b

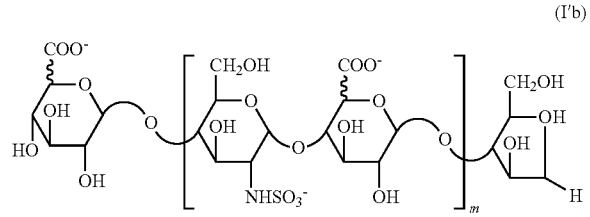

(I'b)

in which X is formyl or, preferably, hydroxymethyl, m is 4, 5 or 6, the corresponding cation is one chemically or pharmaceutically acceptable ion and the glucuronic and iduronic units are present alternately, starting with a glucuronic or iduronic unit. In such case the glucuronic/iduronic ratio is from 45/55 to 55/45, i.e. approximately 50/50.

The use of the C5-epimerase, preferably recombinant, preferably immobilized on a solid support in the conditions shown above therefore allows not the "cluster" epimerization of K5-N-sulfate-derivatives into epiK5-N-sulfate-derivatives as occurs in nature, but the ordinary type.

Thus, according to another of its aspects, the present invention provides the use of the isolated and purified C5-epimerase, for the conversion of a K5-N-sulfate-derivative into a corresponding epiK5-N-sulfate-derivative characterized by a repetitive tetrasaccharide unit consisting of two gliucosamine units separated by a glucuronic unit and followed by an iduronic unit or separated by an iduronic unit and followed by a glucuronic unit.

Said epimerization occurs optimally if carried out on a K5-N-sulfate-derivative having a mean molecular weight of more than 4,000, preferably from 6,000 to 7,500.

According to the present invention, the starting epiK5-N-sulfate-derivatives, preferably 100% N-sulfated (in particular the epiK5-N-sulfate-derivatives consisting of chain mixtures in which at least 90% of said chains have the formula I or I' or in which the preponderant species has the formula I'a or I'b where X is hydroxymethyl), are subjected to the aforesaid steps (a) and (b), upon termination of which are isolated the corresponding, new epiK5-amine-O-oversulfate-derivatives, in which the amine is not substituted, normally in sodium salt form, which can be transformed into another chemically or pharmaceutically acceptable salt. Particularly advantageous salts are those of alkaline metals, alkaline-earth metals, ammonium, ($C_1$-$C_4$)tetraalkylammonium, aluminum and zinc and, among these, the salts of sodium, calcium and tetrabutylammonium are preferred.

Thus, according to another of its aspects, the present invention refers to new epiK5-amine-O-oversulfate-derivatives and their chemically or pharmaceutically acceptable salts, obtainable by a process characterized in that (a) an epiK5-N-sulfate-derivative, in acidic form, is treated with a tertiary or quaternary organic base, letting the reaction mixture to stand for a time period of 30-60 minutes, maintaining the pH of the solution at a value of 7 by addition of said tertiary or quaternary organic base and its salt is isolated with said organic base;

(b) said salt of organic base of said epiK5-N-sulfate-derivative is treated with an O-sulfation reagent in the conditions of O-oversulfation and the epiK5-amine-O-oversulfate-derivative is isolated.

Using, as advantageous starting materials of step (a), epiK5-N-sulfate-derivatives consisting of a chain mixture in which at least 90% of said chains has the aforesaid formula I, in which the uronic units are 20-60% consisting of iduronic acid, n is a integer from 3 to 100 and the corresponding cation is chemically or pharmaceutically acceptable, at the end of step (b) an epiK5-amine-O-oversulfate-derivative is obtained consisting of a chain mixture in which at least 90% of said chains have the formula II

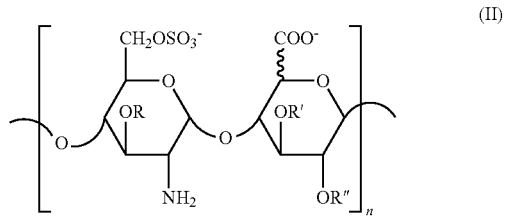

(II)

in which the uronic units are 20-60% consisting of iduronic acid, n is a integer from 2 to 100, preferably from 3 to 100, R, R' and R" are hydrogen or $SO_3$—, for a sulfation degree of at least 3.4, advantageously of at least 3.5, more advantageously from 3.55 to 4, preferably from 3.55 to 3.8 and the corresponding cation is chemically or pharmaceutically acceptable.

These epiK5-amine-O-oversulfate-derivatives with a very high degree of sulfation are new products useful as intermediates in the preparation of their N-sulfate or N—($C_2$-$C_4$) acylated derivatives basically free of activity on the coagulation parameters, but having other interesting pharmacological properties.

Advantageous epiK5-amine-O-oversulfate-derivatives with a very high degree of sulfation are consisting of a chain mixture in which at least 90% of said chains have the formula II in which the uronic units are 40-60% consisting of iduronic acid, n is a integer from 2 to 100, preferably from 3 to 100, with a mean molecular weight from approximately 2,000 to approximately 40,000, advantageously from approximately 4,500 to approximately 40,000, R is at least 40%, preferably 50-80% $SO_3$—, R' and R" are both $SO_3$— or one is hydrogen and the other is 5-10% $SO_3$— in monosulfate glucuronic acid and 10-15% $SO_3$— in monosulfate iduronic acid, the degree of sulfation is more than 3.4, advantageously of at least 3.5, more advantageously from 3.55 to 4, preferably from 3.55 to 3.8, and the corresponding cation is chemically or pharmaceutically acceptable.

Preferred epiK5-amine-O-oversulfate-derivatives with a very high degree of sulfation are LMW-epiK5-amine-O-oversulfates consisting of a chain mixture in which at least 90% of said chains have the formula II in which the uronic units are comprised 40-60%, preferably 50-55%, of iduronic acid, R is at least 40%, advantageously 50-80%, preferably approximately 65% $SO_3$—, R' and R" are both $SO_3$— or one is hydrogen and the other is 5-10% $SO_3^-$ in glucuronic acid and 10-15% $SO_3^-$ in iduronic acid, n is a integer from 2 to 20, advantageously from 3 to 15, with a mean molecular weight from approximately 4,000 to approximately 8,000 and the corresponding cation is chemically or pharmaceutically acceptable.

In practice, said preferred LMW-epiK5-amine-O-oversulfates are consisting of a chain mixture in which at least 90% of said chains have the formula II'

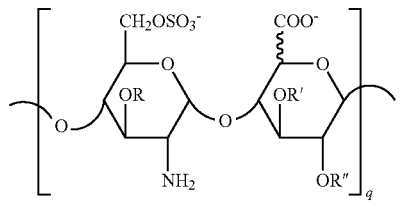

(II')

in which the uronic units are 20-60% consisting of iduronic acid, q is a integer from 2 to 20, advantageously from 3 to 15, R, R' and R" are hydrogen or $SO_3^-$, for a sulfation degree of at least 3.4, advantageously of at least 3.5, more advantageously from 3.55 to 4, preferably from 3.55 to 3.8, and the corresponding cation is one chemically or pharmaceutically acceptable ion.

the chains in said chain mixture, the presence of a 2,5-anhydromannitol sulfated unit of structure (a')

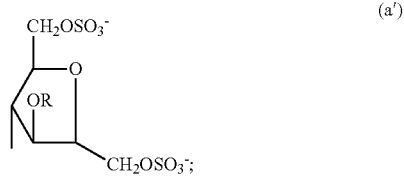

(a')

in which R represents hydrogen or $SO_3^-$.

Thus the reducing end of the majority of the chains in said chain mixture is represented by the structure (b')

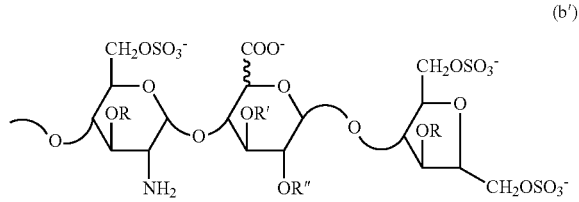

(b')

in which the uronic unit can be glucuronic or iduronic.

Among the aforesaid new LMW-epiK5-amine-O-oversulfates, are preferred those consisting of mixtures in which the preponderant species is a compound of formula II'b

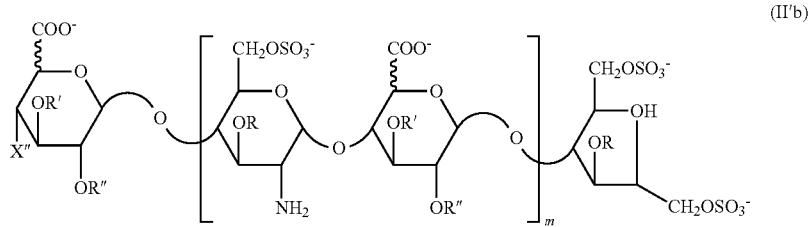

(II'b)

Among these LMW-epiK5-amine-O-oversulfates are preferred those consisting of a chain mixture in which the preponderant species has the formula II'a

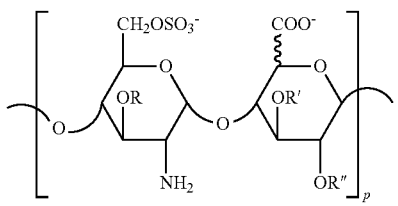

(II'a)

in which the uronic units are 20-60% consisting of iduronic acid, p is a integer from 4 to 8, R, R' and R" are as defined above, the degree of sulfation is at least 3.4, advantageously of at least 3.5, more advantageously from 3.55 to 4, preferably from 3.55 to 3.8 and the corresponding cation is chemically or pharmaceutically acceptable.

The origin of the new LMW-epiK5-amine-O-oversulfates from LMW-epiK5-sulfates obtained by nitrous depolymerization and subsequent reduction with, for example, sodium borohydride, involves, at the reducing end of the majority of in which the uronic units are 40-60% consisting of iduronic acid, m is 4, 5 or 6, R, R' and R" are hydrogen or $SO_3^-$, X" is OH or $OSO_3^-$, for a sulfation degree of at least 3.4, advantageously of at least 3.5, more advantageously from 3.55 to 4, preferably from 3.55 to 3.8, the iduronic units being present alternately, starting with a glucuronic or iduronic unit, and the corresponding cation is one chemically or pharmaceutically acceptable ion.

All these epiK5-amine-O-oversulfated-derivatives with a very high degree of sulfation are new products which are useful intermediates for the preparation of the new N-substituted epiK5-amine-O-oversulfated-derivatives and therefore constitute an additional aspect of the present invention.

In particular, according to another of its aspects, the invention concerns the use of the aforesaid epiK5-amine-O-oversulfated-derivatives with a very high degree of sulfation for the preparation of new N-substituted epiK5-amine-O-oversulfated-derivatives, in particular N-sulfated or N-acylated.

Upon termination of step (c) of the process of the present invention, consisting of an N-sulfation of the epiK5-amine-O-oversulfate-derivatives obtained at the end of step (b) (in particular the epiK5-amine-O-oversulfate-derivatives consisting of chain mixtures in which at least 90% of said chains have the formula II or II' or in which the preponderant species has the formula II'a or II'b) epiK5-N,O-oversulfate-derivatives are obtained whose iduronic acid content is 20-60% of the total of the uronic acids and whose sulfation degree is at least 4, preferably from 4 to 4.6.

Thus, according to another of its aspects, the present invention provides new N-deacetylated derivatives of K5 polysaccharide, O-sulfated and N-sulfated, C5-epimerized to iduronic acid in at least 20% of the total of the uronic units, having a mean molecular weight from approximately 2,000 to approximately 45,000, a sulfation degree of at least 4, said derivatives being basically inactive on the coagulation parameters.

Similarly to that stated above, said new derivatives are, as a whole, denoted by the general term "epiK5-N,O-oversulfate-derivatives", independently of their molecular weight.

In particular, the mean molecular weight is between approximately 2,000 to approximately 45,000 since said derivatives originate either from an epi-K5-N-sulfate obtained by N-deacetylation and N-sulfation of K5 by fermentation or by the nitrous depolymerization of the latter. By controlling said nitrous depolymerization it is possible to obtain low molecular weight derivatives in virtually all the aforesaid interval. However, for use of the derivatives of the present invention as pharmaceutical or cosmetic products it is advantageous to prepare low molecular weight derivatives, with a mean molecular weight from approximately 2,000 to approximately 16,000, advantageously from approximately 3,500 to approximately 13,000 with a molecular weight distribution of between approximately 1,000 and approximately 15,000, preferably from approximately 4,500 to approximately 9,000, with a molecular weight distribution from approximately 2,000 to approximately 10,000, or of high molecular weight derivatives, originating from the unfractionated K5, with a mean molecular weight of between approximately 20,000 and approximately 45,000, with a molecular weight distribution from approximately 2,000 to approximately 70,000.

In the epiK5-N,O-oversulfate-derivatives of the present invention the degree of sulfation is very high, preferably from 4 to 4.6, the nitrogen of the glucosamine being virtually 100% sulfated. Besides, the epiK5-N,O-oversulfate-derivatives are 100% 6-O-sulfated and 50-80% 3-O-sulfated in their gliucosamine units, 5-10% 3-O-monosulfated in glucuronic units, 10-15% O-monosulfated in iduronic units and 2.3-di-O-sulfated in the remaining uronic units, considering that the degree of sulfation is at least 4.

Advantageous epiK5-N,O-oversulfate-derivatives according to the present invention are obtained through epiK5-amine-O-oversulfate-derivatives in turn prepared from epiK5-N-sulfate-derivatives consisting of a chain mixture in which at least 90% of said chains has the aforesaid formula I, in which the uronic units are 20-60% consisting of iduronic acid, n is a integer from 2 to 100, advantageously from 3 to 100 and the corresponding cation is chemically or pharmaceutically acceptable.

In such case, the new epiK5-N,O-oversulfate-derivatives consisting of chain mixtures in which at least 90% of said chains have the formula III

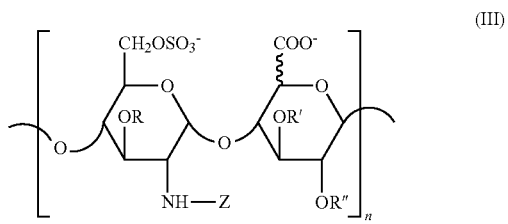

in which the uronic units are 20-60% consisting of iduronic acid, n is a integer from 2 to 100, preferably from 3 to 100, R, R' and R" are hydrogen or $SO_3$—, Z is $SO_3$, the degree of sulfation is at least 4, preferably from 4 to 4.6 and the corresponding cation is chemically or pharmaceutically acceptable.

Said cations are advantageously those of alkaline metals, alkaline-earth metals, ammonium, $(C_1$-$C_4)$tetraalkylammonium, aluminum and zinc and, among these, preferably the salts of sodium, calcium and tetrabutylammonium.

Among the aforesaid new epiK5-amine-N,O-oversulfate-derivatives, those consisting of chain mixtures in which at least 90% of said chains has the aforesaid formula III in which R is $SO_3$— in 50%-80%, preferably in approximately 65% of said chains and the degree of sulfation is at least 4, advantageously is from 4 to 4.6, preferably from 4 to 4.3. Advantageous epiK5-N,O-oversulfate-derivatives with a very high degree of sulfation are consisting of a chain mixture in which at least 90% of said chains have the formula III, in which Z is $SO_3$—, the uronic units are 40-60% consisting of iduronic acid, n is a integer from 2 to 100, preferably from 3 to 100, with a mean molecular weight from approximately 2,000 to approximately 45,000, advantageously from approximately 4,500 to approximately 45,000, R is at least 40%, preferably 50-80% $SO_3$—, R' and R" are both $SO_3$— or one is hydrogen and the other is 5-10% $SO_3$— in monosulfate glucuronic acid and 10-15% $SO_3$— in monosulfate iduronic acid, the degree of sulfation is at least 4, from to 4.6 and the corresponding cation is chemically or pharmaceutically acceptable.

Preferred N-substituted epiK5-amine-O-oversulfated-derivatives are LMW-epiK5-amine-O-oversulfated consisting of a chain mixture in which at least 90% of said chains have the formula III in which the uronic units are 40-60% comprised, preferably 50-55%, of iduronic acid, R is at least 40%, advantageously 50-80%, preferably approximately 65% $SO_3$—, R' and R" are both $SO_3$— or one is hydrogen and the other is 5-10% $SO_3$— in glucuronic acid and 10-15% $SO_3$— in iduronic acid, Z is 100% $SO_3$— or (C2-C4)acyl, n is a integer from 2 to 20, preferably from 3 to 15, with a mean molecular weight from approximately 4,000 to approximately 8,500 and the corresponding cation is chemically or pharmaceutically acceptable.

In practice, said preferred epiK5-N,O-sulfate-derivatives with a very high degree of sulfation are consisting of a chain mixture in which at least 90% of said chains have the formula III'

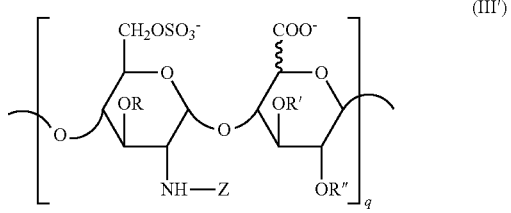

(III')

in which the uronic units are 20-60% consisting of iduronic acid, q is a integer from 2 to 20, advantageously from 3 to 15, R, R' and R" represent hydrogen or an $SO_3^-$ group, Z is $SO_3^-$, for a sulfation degree of at least 4, preferably from 4 to 4.6 and the corresponding cation is one chemically or pharmaceutically acceptable ion.

Particularly interesting are chain mixtures of formula III' in which the uronic units are 40-60% comprised, preferably 50-55%, of iduronic acid, R is at least 40%, advantageously 50-80%, preferably approximately 65% $SO_3^-$, R' and R" are both $SO_3^-$ or one is hydrogen and the other is 5-10% $SO_3^-$ in glucuronic acid and 10-15% $SO_3^-$ in iduronic acid, n is a integer from 2 to 20, advantageously from 3 to 15, with a mean molecular weight from approximately 2,000 to approximately 16,000, advantageously from approximately 3,500 to approximately 13,000, preferably from approximately 4,500 to approximately 9,000 and the corresponding cation is chemically or pharmaceutically acceptable.

Among these LMW-epiK5-N,O-oversulfates, are advantageous those consisting of a chain mixture in which the preponderant species has the formula III'a

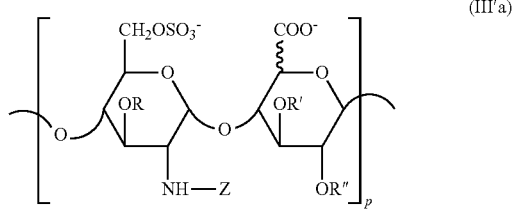

(III'a)

in which the uronic units are 20-60% consisting of iduronic acid, p is a integer from 4 to 8, Z is $SO_3^-$, R, R' and R" are hydrogen or $SO_3^-$, for a sulfation degree of at least 4, preferably from 4 to 4.6 and the corresponding cation is chemically or pharmaceutically acceptable.

The origin of the new LMW-epiK5-N,O-oversulfates from LMW-epiK5-sulfates obtained by nitrous depolymerization and subsequent reduction with, for example, sodium borohydride involves, at the reducing end of the majority of the chains in said chain mixture, the presence of a sulfated 2,5-anhydromannitol unit of structure (a') as shown above, in which R represents hydrogen or $SO_3^-$.

Thus, the reducing end of the majority of the chains in said chain mixture is represented by the structure (b")

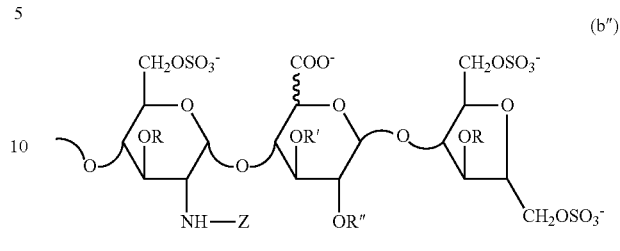

(b")

in which Z represents $SO_3^-$ and the uronic unit can be glucuronic or iduronic.

Among the aforesaid new LMW-epiK5-N,O-oversulfates, are preferred those consisting of mixtures in which the preponderant species is a compound of formula III'b

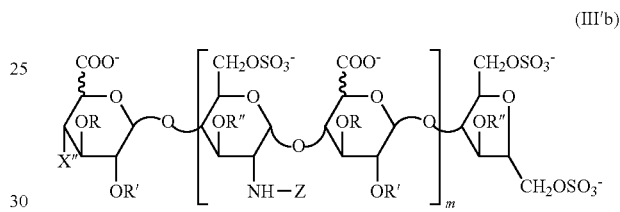

(III'b)

in which R, R' and R" are hydrogen or $SO_3^-$, Z is $SO_3^-$, X" is OH or $OSO_3^-$, m is 4, 5 or 6, for a sulfation degree of at least 4, preferably from 4 to 4.6, the uronic units are present alternately, starting with a glucuronic or iduronic unit, and the corresponding cation is one chemically or pharmaceutically acceptable ion. Said cations are advantageously those of alkaline metals, alkaline-earth metals, ammonium, $(C_1-C_4)$tetraalkylammonium, aluminum and zinc and, among these, preferably the ions of sodium, calcium and tetrabutylammonium.

If an epiK5 is used as a starting epiK5-derivative of the process of the present invention, i.e. a K5 polysaccharide, previously N-deacetylated, N-sulfated normally 100%, and 20-60% C5-epimerized and not depolymerized, upon termination of step (c) an epiK5-N,O-oversulfate is isolated which can be subjected to nitrous depolymerization and possible, subsequent reduction with, for example, sodium borohydride to obtain the corresponding LMW-epiK5-N,O-oversulfate having the same degree of sulfation. In particular, LMW-epiK5-N,O-oversulfates are obtained consisting of a chain mixture in which at least 90% of said chains have the formula III' or III'a, in which the uronic units are 20-60% consisting of iduronic acid, q, R, R' R" and Z have the meaning defined above, for a sulfation degree of at least 4, preferably from 4 to 4.6 and the corresponding cation is one chemically or pharmaceutically acceptable ion. In such case, the origin of these LMW-epiK5-N,O-oversulfates from a depolymerization reaction and possible, subsequent reduction with, for example, sodium borohydride involves, at the reducing end of the majority of the chains in said chain mixture, the presence of a 2,5-anhydromanno unit of structure (a″)

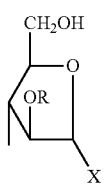

(a″)

in which X is formyl or hydroxymethyl and R represents hydrogen or $SO_3^-$.

The new epiK5-N,O-oversulfate-derivatives, especially in their salt form, are highly anionic products able to capture the free radicals and are utilizable in the cosmetics industry as adjuvants against hair loss or to prepare "anti-ageing" creams and, in the pharmaceutical industry, as products for the treatment of dermatitis. Besides, the epiK5-N,O-oversulfate-derivatives of the present invention, in particular the LMW-epiK5-N,O-oversulfates possess antiangiogenetic and antiviral activity and therefore constitute active ingredients for the preparation of medicines.

Thus, according to one of its additional aspects, the present invention provides pharmaceutical compositions including, as one of their active ingredients, a pharmacologically active amount of an epiK5-N,O-oversulfate-derivative as shown above or of one of its pharmaceutically acceptable salts, in mixture with a pharmaceutical excipient.

In the pharmaceutical compositions of the present invention for oral, subcutaneous, intravenous, transdermal or topical administration, the active ingredients are preferably administered in the form of dosage units, in mixture with the classic pharmaceutical excipients or vehicles. The posology can vary widely depending on the age, weight, and the health condition of the patient. This posology includes the administration of a dose from 1 to 1000 mg, advantageously from 10 to 750 mg, preferably 250 to 500 mg from one to three times a day by intravenous, subcutaneous, oral, transdermal or topical administration. The pharmaceutical compositions of the present invention are formulated with the classic excipients suitable for different ways of administration. Particularly advantageous are the formulations in the form of creams, ointments, liniments, gels, foams, balsams, vaginal pessaries, suppositories, solutions or suspensions suitable for local administration.

Advantageously, the compositions of the present invention include, as one of its active ingredients, an epiK5-N,O-oversulfate-derivative obtainable starting with an epiK5-derivative according to steps (a), (b) and (c) of the process described above, or starting with an epiK5 not depolymerized, according to steps (a), (b) and (c) of the process described above, with possible subsequent nitrous depolymerization after step (c), or one of its pharmaceutically acceptable salts, in mixture with a pharmaceutical excipient. Advantageously, said epiK5-N,O-oversulfate-derivative consists of a chain mixture in which at least 90% of said chains have the formula III or III' or in which the preponderant species is a compound of formula III'a or III'b. Preferred active ingredient is a LMW-epiK5-N,O-oversulfate having a sulfation degree of at least 4, preferably from 4 to 4.6, advantageously having a mean molecular weight from approximately 3,500 to approximately 11,000, more advantageously from approximately 3,500 to approximately 5,200 and basically free of N-acetyl groups.

Finally, according to another of its aspects, the present invention provides a cosmetic composition including an effective amount of an epiK5-N,O-oversulfate-derivative or one of its pharmaceutically acceptable salts, in mixture with a cosmetic excipient.

A salt selected from the group consisting of salts of sodium, potassium, calcium, magnesium, aluminum and zinc of the epiK5-N,O-oversulfate derivatives, in particular those consisting of chain mixtures in which at least 90% of said chains have the formula III or III' or in which the preponderant species has the formula III'a or III'b, constitutes an effective active ingredient of the pharmaceutical or cosmetic compositions of the present invention.

The following examples illustrate the invention without however limiting it.

Preparation I

Preparation of K5 Polysaccharide from *Escherichia coli*

At first fermentation is carried out in an Erlenmeyer flask using the following medium:

| | |
|---|---:|
| Fat-free soya meal | 2 g/l |
| $K_2HPO_4$ | 9.7 g/l |
| $KH_2PO_4$ | 2 g/l |
| $MgCl_2$ | 0.11 g/l |
| Sodium citrate | 0.5 g/l |
| Ammonium sulfate | 1 g/l |
| Glucose | 2 g/l |
| Spring water | 1000 ml | pH = 7.3

The medium is sterilized at 120° C. for 20 minutes. The glucose is prepared separately in solution form which is sterilized at 120° C. for 30 minutes and added sterilely to the medium. The Erlenmeyer flask is inoculated with a suspension of *E. coli* cells Bi 8337/41 (O10:K5:H4) originating from a slant kept in Triptic soy agar, and incubated at 37° C. for 24 hours under controlled agitation (160 rpm, 6 cm stroke). The bacterial growth is measured by counting the cells using a microscope. In a subsequent operation, a 14 l Chemap-Braun fermenter containing the same medium as above, is 0.1% inoculated with the culture of the Erlenmeyer flask as above and fermentation is performed by aeration of 1 vvm, (vvm=volume of air per volume of liquid per minute) 400 rpm agitation and temperature of 37° C. for 18 hours. During fermentation are measured the pH, the oxygen, the glucose residue, K5 polysaccharide produced and bacterial growth. At the end of fermentation the temperature is brought to 80° C. for 10 minutes. The cells are separated from the medium through centrifugation at 10,000 rpm and the supernatant is ultrafiltered using an SS 316 (MST) module fitted with PES membrane with nominal cut-off of 800 and 10,000 D to reduce the volume to ⅕. K5 polysaccharide is then precipitated by addition of 4 volumes of acetone at 4° C. and left to settle overnight at 4° C. Finally it is recovered by centrifugation at 10,000 rpm for 20 minutes or filtration. Deproteinization of the solid obtained is carried out by using a type II protease from *Aspergillus orizae* in a buffer of 0.1 M NaCl and 0.15 M EDTA at pH 8 containing SDS (0.5% sodium dodecyl sulfate) (10 mg/l of filtrate) at 37° C. for 90 minutes. The solution obtained is ultrafiltered on model SS 316 with membrane at a nominal cut-off of 10,000 D with 2 extractions with 1M NaCl and washed with water until disappearance of absorbance in the ultrafiltrate. K5 polysaccharide is then precipitated with acetone and a yield of 850 mg per litre of fermenter is obtained. The purity of the polysaccharide obtained is measured through the determination of the uronic acids (carbazole method), proton and carbon 13 NMR, UV and protein content. The purity is more than 80%.

The polysaccharide obtained is composed of two moieties of different molecular weight, respectively 30,000 and 5,000 D as emerges from the determination by HPLC using a Pharmacia 75 HR column and a single moiety with a retention time of approximately 9 minutes using two sedate columns of Bio-sil SEC 250 (Bio Rad) and $Na_2SO4$ as mobile phase at room temperature and a flow of 0.5 ml/minute. The measurement is performed against a standard curve obtained with moieties of heparin of known molecular weight.

The $^1$H-RMN spectrum of the purified K5 thus obtained shows different signals attributable to methyls of lipophilic substances.

Preparation II
Purification of K5

In 100 ml of a saturated aqueous solution of sodium chloride and thermostated at 4° C. is dissolved 1 g of K5 obtained at the end of PREPARATION I and to the solution thus obtained are added 3 volumes of cold isopropanol. The saline concentration of the solution is brought to 3 M by addition of the calculated amount of a saturated sodium chloride solution and the solution obtained is left in a cold environment (approximately 4° C.) overnight. The precipitate which forms is separated by centrifugation at 10,000 rpm for 20 minutes and the purity of the product is checked by dialysis overnight and subsequent examination of the $^1$H-RMN spectrum, from which signals in the region under 1.5 ppm must be absent. Optionally, the operation of dissolution in water saturated with NaCl and precipitation with isopropanol is repeated. The precipitate is dissolved in water and ultrafiltered on a Miniplate Millipore membrane 10,000 D cut off until disappearance of the salts. Thus a K5 having a purity of at least 99% is obtained from whose $^1$H-RMN spectrum no traces of lipophilic impurities result in the region under 1.5 ppm.

Preparation III
Preparation of a K5-N-Sulfate
(i) N-Deacetylation

Ten grams of pure K5 polysaccharide prepared as described in PREPARATION II are dissolved in 1000 ml of 2N sodium hydroxide and the solution thus prepared is left at 60° C. for 24 hours. The solution is brought to room temperature then to neutral pH (pH7) with 6N hydrochloric acid.

(ii) N-Sulfation

To the solution containing the deacetylated K5, kept at 40° C., are added 16 g of sodium carbonate and afterwards and in 4 hours, 16 g of pyridine.$SO_3$—. At the end of the reaction, after 24 hours, the solution is brought to room temperature, then to pH 6.5-7 with a 5% solution of hydrochloric acid. The product is purified from salts by diafiltration using a 1,000 D helically wound membrane (prepscale cartridge-Millipore). The process is terminated when the conductivity of the permeate is less than 1000 μS, preferably less than 100 μS. The intradialysis is reduced until a 10% concentration of the polysaccharide is obtained using the same in concentration dialysis system. The concentrated solution is dried by lyophilization. Upon $^{13}$C-RMN spectrum analysis N-acetyl or $NH_2$ residues do not appear.

Preparation IV
LMW-K5-N-Sulfate

The product obtained as described in Example 1, steps (i) and (ii), of WO 02/068477 is depolymerized by the degradation method with nitrous acid and subsequent reduction of the aldehyde which forms. One continues by dissolving 1 g of K5-N-sulfate in 200 ml of distilled water and adding it with 480 mg of sodium nitrite dissolved in 240 ml of distilled water. The solution is then brought to 4° C. and the pH to 2 with 0.1 N HCl and maintained for 30 minutes. At the end of the reaction the solution is brought to pH 7 with 0.1 M NaOH and then to room temperature. The solution is then added with 450 mg. of $NaBH_4$ and left to react for 4 hours. The excess $NaBH_4$ is eliminated with HCl bringing the pH to 5-6. The product, neutralized with 0.1 M NaOH, is recovered by precipitation with 3 volumes of acetone at 4° C., filtration with filtering funnel and dried at 40° C. in a vacuum oven. 900 mg of LMW-K5-N-sulfate are obtained with a mean molecular weight of approximately 2,000, consisting of a chain mixture in which the preponderant species is a compound of formula I'b in which m is 4 and the uronic units are those of glucuronic acid.

Example 1

LMW-epiK5-N-sulfate

Sequence (i)→(ii)

(i) Epimerization to epiK5-N-Sulfate

Ten grams of K5-N-sulfate obtained as described in Example 1, steps (i) and (ii), of WO 02/068477, from whose $^1$H-RMN spectrum, signals concerning acetyl groups or $NH_2$ do not appear, are dissolved in 600 ml of 25 mM HEPES buffer at pH 7, containing $CaCl_2$ at a concentration of 50 mM and the solution thus obtained is made to recirculate through a 50 ml column filled with Sepharose 4B resin containing 5 g of recombinant C5-epimerase (WO 96/14425) immobilized as described in Example 1 of WO 01/72848. The reaction is carried out at 30° C. at pH 7 with a flow of 200 ml/h for 24 hours. The product obtained is purified by ultrafiltration and precipitation with ethanol. Thus an epiK5-N-sulfate is obtained whose iduronic acid content is 54%.

(ii) Depolymerization of epiK5-N-Sulfate.

To a solution of 1 g of the product thus obtained, in 25 ml of distilled water, are added 230 mg of sodium nitrite dissolved in 115 ml of distilled water. The solution is then brought to 4° C. and the pH to 2 with 0.1 N HCl and maintained for 30 minutes. At the end of the reaction the solution is brought to room temperature and the pH to 7 with 0.1 M NaOH. The solution is then added with 450 mg. of $NaBH_4$ and left to react for 4 hours. The product is recovered by precipitation with 3 volumes of acetone at 4° C., filtration with filtering funnel and dried at 40° C. in a vacuum oven. 900 mg of LMW-epiK5-N-sulfate are obtained with an iduronic acid content of 54% and a molecular weight distribution from 1,000 to 4,000, measured with HPLC method.

Example 2

LMW-epiK5-N-sulfate

Sequence (ii)→(i)

(ii) Depolymerization of K5-N-Sulfate 2 g of K5-N-sulfate, obtained as described in Example 1, steps (i) and (ii), of WO 02/068477, is depolymerized as described in PREPARATION I, using 100 mg of sodium nitrite and 300 mg of sodium borohydride. 1.8 g of LMW-K5-N-sulfate are obtained with a mean molecular weight of 5,000.

(i) Epimerization of LMW-K5-N-Sulfate 1 g of LMW-K5 N-sulfate obtained in step (ii) herein above is treated as described in step (i) of the Example 1. An epimerized product is obtained with an iduronic acid/glucuronic acid ratio of 44/56 against a ratio of 0/100 of the starting product, with a molecular weight distribution from 2,000 to 10,000 and with a mean molecular weight of 5,000 D. The yield, calculated by measuring the content of uronic acids against a standard with the carbazole method (Bitter and Muir, Anal. Biochem. 1971, 39, 88-92) is 90%.

Example 3

LMW-epiK5-N-sulfate

Sequence (i)→(ii)

(i) Epimerization of K5-N-Sulfate

A 2 g amount of K5 N-sulfate, obtained as described in Example 1, steps (i) and (ii), of WO 02/068477, is dissolved in 120 ml of 25 mM HEPES buffer, pH 7, containing 50 mM $CaCl_2$. The solution obtained is made to recirculate through a 50 ml column filled with the resin containing the immobilized enzyme obtained as described in WO 96/14425. This operation is carried out at 30° C. with a flow of 200 ml/h for 24 hours. The product obtained is purified through ultrafiltration on a 1000 D membrane and passing over an IR 120 $H^+$ ionic exchange column, neutralizing the eluate with 1N NaOH. The sample is recovered by precipitation with ethanol or acetone. An epimerized product is obtained with an iduronic acid/glucuronic acid ratio of 55/45 against a ratio of 0/100 of the starting product. The percentage of epimerization was calculated with $^1$H-RMN according to the method described in WO 96/14425. The yield, calculated by measuring the content of uronic acids against a standard with the carbazole method (Bitter and Muir Anal. Biochem. 39, 88-92-1971) is 90%.

(ii) Depolymerization of epi-K5-N-Sulfate

One gram of product obtained in step (a) is depolymerized by the degradation method with nitrous acid and subsequent reduction of the aldehyde which forms. In particular one continues by dissolving the product in 25 ml of distilled water and adding it with 230 mg of sodium nitrite dissolved in 115 ml of distilled water. The solution is then brought to 4° C. and the pH to 2 with 0.1 N HCl and maintained for 30 minutes. At the end of the reaction the solution is brought to room temperature and the pH to 7 with 0.1 M NaOH. The solution is then added with 450 mg. of $NaBH_4$ and left to react for 4 hours. The product is recovered by precipitation with 3 volumes of acetone at 4° C., filtration with filtering funnel and dried at 40° C. in a vacuum oven. 900 mg of LMW-epiK5-N-sulfate are obtained with a molecular weight distribution measured with HPLC method which ranges from 1,000 to 4,000 and with a glucuronic unit content of 45% and an iduronic unit content of 55%.

Example 4

EpiK5-N,O-oversulfate (a) Tetrabutylammonium Salt of epiK5-N-Sulfate

A solution in 40 ml of water of 400 mg of epiK5-N-sulfate, as obtained at the end of step (i) of the Example 1, is thermostated at 4° C., then passed over IR 120$^+$ ionic exchange resin preconditioned with water at 4° C. The eluate obtained, consisting of 100 ml of a solution at pH 1.94, is neutralized with a 15% solution of tetrabutylammonium hydroxide and left at room temperature for one hour, maintaining the pH at 7 by addition of 15% tetrabutylammonium hydroxide and finally is lyophilized. Thus 805 mg of tetrabutylammonium salt of epiK5-N-sulfate are obtained.

(b) Epi-K5-Amine-O-Oversulfate

A solution containing 805 mg of the salt thus obtained in 30 ml of dimethylformamide is set at 55° C. and treated with 30 ml of dimethylformamide containing 2.26 g of pyridine.$SO_3$ adduct. The reaction at 55° C. is continued overnight then 60 ml of water are added to the mixture. After neutralization with 1 N NaOH, the product is precipitated with 3 volumes of acetone saturated with NaCl and set at 4° C. overnight. The precipitate is recovered by filtration on such G4 and then ultrafiltered with 1000 D TFF Millipore system and dried at reduced pressure. 550 mg of epi-K5-amine-O-oversulfated are obtained having a content of iduronic acid of 54%, of glucosamine-6-O-sulfate of 100%, of glucosamine 3-O-sulfate of 60%, of monosulfate glucuronic acid of 10%, of monosulfate iduronic acid of 15%, the rest of the uronic units being disulfated, with a sulfation degree of 3.55 measured with the conductometric method according to Casu et al. 1975.

(c) EpiK5-Amine-O-Oversulfated-N-Sulfate

To a solution of 250 mg of the epi-K5-amine-O-oversulfated obtained in step (b) in 15 ml of water are added 400 mg of sodium carbonate, then to the mixture thus obtained are added 400 mg of pyridine.$SO_3$ adduct in solid form a little at a time in 4 hours. The reaction mixture is kept at 55° C. overnight, then is stopped bringing the pH to 7 with 0.1 N HCl. After ultrafiltration on a 1000 D membrane are added 3 volumes of acetone saturated with sodium chloride and the precipitate is recovered by centrifugation at 5000 rpm for 5'. Thus 244 mg of epiK5-N,O-oversulfate are obtained whose sulfation degree, measured with conductometric method according to Casu et al. 1975, is 4.25. By the analysis of the $^1$H-RMN spectrum it results that the epiK5-N,O-oversulfate thus obtained has an iduronic acid content of 54%, 6-O-sulfate of 100%, N-sulfate of 100%, glucosamine 3-O-sulfate of 60%, monosulfate glucuronic acid of 10%, monosulfate iduronic acid of 15%, the rest of the uronic units being disulfated. From the $^1$H-RMN spectrum is therefore calculated a sulfation degree of 4.35 which, considering the margins of error of the methods, corresponds to the sulfation degree of epiK5-amine-O-oversulfated obtained upon termination of step (b), 100% N-sulfated. It is therefore assumed that, beyond a certain percentage of sulfate groups, the strong anionic nature of the product can lead to an underestimation of the degree of sulfation determined with the conductometric method.

What is claimed is:

1. An epiK5-amine-O-oversulfate-derivative consisting of a chain mixture in which at least 90% of said chains have the formula II

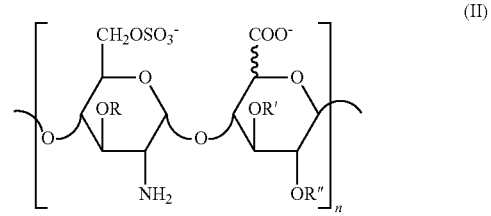

in which the uronic units are 20-60% consisting of iduronic acid, n is an integer from 2 to 100, R, R' and R" are hydrogen or $SO_3^-$, the degree of sulfation is from 3.55 to 4 and the corresponding cation is chemically or pharmaceutically acceptable.

2. An epiK5-amine-O-oversulfate-derivative according to claim 1, wherein n is an integer from 3 to 100.

3. An epiK5-amine-O-oversulfate-derivative according to claim 1, consisting of a chain mixture in which at least 90% of said chains have the formula II in which the uronic units are 40-60% consisting of iduronic acid, the mean molecular weight is from approximately 2,000 to approximately 40,000, R is at least 40%, $SO_3^-$, R' and R" are both $SO_3^-$ or one is hydrogen and the other is 5-10% $SO_3^-$ in monosulfate glucuronic acid and 10-15% $SO_3^-$ in monosulfate iduronic acid.

4. An epiK5-amine-O-oversulfate-derivative according to claim 1, which is a LMW-epiK5-amine-O-oversulfate consisting of a chain mixture in which at least 90% of said chains have the formula II in which the uronic units are 40-60% consisting of iduronic acid, R is at least 40%, $SO_3^-$, R' and R" are both $SO_3^-$ or one is hydrogen and the other is 5-10% $SO_3^-$ in glucuronic acid and 10-15% $SO_3^-$ in iduronic acid, n is an integer from 3 to 15, the mean molecular weight from approximately 4,000 to approximately 8,000 and the corresponding cation is chemically or pharmaceutically acceptable.

* * * * *